(12) United States Patent
Huffman

(10) Patent No.: US 6,884,068 B2
(45) Date of Patent: Apr. 26, 2005

(54) DENTAL MODEL BASE CONFIGURED FOR CUSTOMIZED APERTURE FORMATION

(76) Inventor: Ronald E. Huffman, 13644 N. Placita Montanas De Oro, Oro Valley, AZ (US) 85737

(*) Notice: Subject to any disclaimer, the term of this patent is extended or adjusted under 35 U.S.C. 154(b) by 154 days.

(21) Appl. No.: 10/098,905

(22) Filed: Mar. 13, 2002

(65) Prior Publication Data

US 2002/0164556 A1 Nov. 7, 2002

Related U.S. Application Data

(63) Continuation-in-part of application No. 09/349,192, filed on Jul. 7, 1999, now abandoned.

(51) Int. Cl.$^7$ .............................................. A61C 11/00
(52) U.S. Cl. ........................................ 433/60; 433/34
(58) Field of Search ............................ 433/54, 57, 60, 433/64, 34

(56) References Cited

U.S. PATENT DOCUMENTS

| 921,791 A | 5/1909 | Benson |
|---|---|---|
| 967,086 A | 8/1910 | Tuttle |
| 1,013,028 A | 12/1911 | Lee |
| 1,745,570 A | 2/1930 | Dimelow |
| 1,772,027 A | 8/1930 | Baumgarten |
| 1,780,117 A | 10/1930 | Craigo |
| 2,398,671 A | 4/1946 | Saffir |
| 2,585,857 A | 2/1952 | Schwartz |
| 2,842,845 A | 7/1958 | Carlson |
| 3,453,736 A | 7/1969 | Waltke |
| 3,478,428 A | 11/1969 | Stengel |
| 3,510,947 A | 5/1970 | Tuccillo |
| 3,518,761 A | 7/1970 | Susman et al. |
| 3,581,398 A | 6/1971 | Thomas |
| 3,934,348 A | 1/1976 | Janjic |
| 3,937,773 A | 2/1976 | Huffman |
| 3,969,820 A | 7/1976 | Kulig et al. |
| 4,021,916 A | 5/1977 | Spalten |
| 4,022,419 A | 5/1977 | Haker |
| 4,116,416 A | 9/1978 | Segura |
| 4,122,606 A | 10/1978 | Roman |
| 4,127,939 A | 12/1978 | Samuel et al. |
| 4,203,219 A | 5/1980 | Wiener |
| 4,240,605 A | 12/1980 | Waltke |
| 4,242,812 A | 1/1981 | Randoll et al. |
| 4,265,619 A | 5/1981 | Lucki et al. |
| 4,283,173 A | 8/1981 | Browne et al. |
| 4,301,357 A | 11/1981 | Huffman |
| 4,319,875 A | 3/1982 | Beckwith |
| 4,359,464 A | 11/1982 | Weinstock |
| 4,371,339 A | 2/1983 | Zeiser |

(Continued)

FOREIGN PATENT DOCUMENTS

| DE | 34 36 094 | 3/1985 |
|---|---|---|
| DE | 35 05 680 | 7/1985 |
| DE | 35 21 137 | 12/1986 |
| DE | 38 25 014 | 1/1990 |
| EP | 0 151 086 | 8/1985 |
| EP | 0 210 484 | 2/1987 |
| EP | 0 291 821 | 11/1988 |
| EP | 0 528 335 | 2/1993 |
| EP | 0 277 026 A2 | 8/1998 |
| FR | 2 750 851 A1 | 1/1998 |
| GB | 866118 | 4/1961 |
| WO | WO 88/10101 | 12/1988 |
| WO | WO 97/16130 A1 * | 5/1997 ............ A61C/9/00 |

*Primary Examiner*—Todd E. Manahan
(74) *Attorney, Agent, or Firm*—Merchant & Gould PC

(57) ABSTRACT

A premanufactured dental model base, and method, for supporting a cast dental model. The dental model base has a dental model support surface adapted such that a user may create apertures in the dental model support surface. The apertures are adapted to receive pins that secure the dental model to the dental model base and for disengagably retaining a dental model segment representing a damaged tooth.

29 Claims, 11 Drawing Sheets

U.S. PATENT DOCUMENTS

| | | | |
|---|---|---|---|
| 4,378,929 A | 4/1983 | Huffman | |
| 4,382,787 A | 5/1983 | Huffman | |
| 4,398,884 A | 8/1983 | Huffman | |
| 4,439,151 A | 3/1984 | Whelan | |
| 4,443,192 A | 4/1984 | Blitz | |
| 4,449,930 A | 5/1984 | Huffman | |
| 4,449,931 A | 5/1984 | Saito | |
| 4,459,110 A | 7/1984 | Jackson | |
| 4,473,353 A | 9/1984 | Greggs | |
| 4,481,162 A | 11/1984 | Huffman | |
| 4,494,934 A | 1/1985 | Huffman | |
| 4,521,188 A | 6/1985 | Metzler | |
| 4,533,323 A | 8/1985 | Huffman | |
| 4,538,987 A | 9/1985 | Weissman | |
| 4,548,581 A | 10/1985 | Huffman | |
| D283,541 S | 4/1986 | Huffman | |
| D283,542 S | 4/1986 | Huffman | |
| D283,639 S | 4/1986 | Huffman | |
| D283,730 S | 5/1986 | Huffman | |
| 4,608,016 A | 8/1986 | Zeiser | |
| D286,179 S | 10/1986 | Huffman | |
| D286,436 S | 10/1986 | Huffman | |
| 4,645,454 A | 2/1987 | Amdur et al. | |
| D289,924 S | 5/1987 | Huffman | |
| 4,671,770 A | 6/1987 | Bell et al. | |
| 4,708,648 A | 11/1987 | Weissman | |
| 4,708,835 A | 11/1987 | Kiefer | |
| 4,721,464 A | 1/1988 | Roden et al. | |
| 4,734,033 A | 3/1988 | Huffman | |
| 4,767,330 A | 8/1988 | Burger | |
| 4,767,331 A | 8/1988 | Hoe | |
| 4,786,253 A | 11/1988 | Morais | |
| 4,834,651 A | 5/1989 | Fenick | |
| 4,842,242 A | 6/1989 | Huffman | |
| D302,587 S | 8/1989 | Huffman | |
| D302,724 S | 8/1989 | Huffman | |
| D302,725 S | 8/1989 | Huffman | |
| RE33,099 E | 10/1989 | Shoher et al. | |
| D305,361 S | 1/1990 | Huffman | |
| D305,362 S | 1/1990 | Huffman | |
| D306,206 S | 2/1990 | Huffman | |
| 4,898,359 A | 2/1990 | Gopon | |
| RE33,271 E | 7/1990 | Shoher et al. | |
| 4,940,409 A | 7/1990 | Nordin | |
| 5,028,235 A | 7/1991 | Smith | |
| 5,049,075 A | 9/1991 | Barrut | |
| 5,098,290 A | 3/1992 | Honstein et al. | |
| 5,100,317 A | 3/1992 | Darnand | |
| 5,197,874 A | 3/1993 | Silva et al. | |
| 5,207,574 A | 5/1993 | Garland | |
| 5,352,117 A | * 10/1994 | Silva | 433/60 |
| 5,393,227 A | 2/1995 | Nooning | |
| 5,403,185 A | * 4/1995 | Presswood | 433/74 |
| 5,466,152 A | 11/1995 | Walter | |
| 5,470,231 A | 11/1995 | Stern | |
| 5,501,600 A | 3/1996 | Johnson | |
| 5,766,007 A | 6/1998 | Huffman | |
| 5,769,634 A | 6/1998 | Choi | |
| 5,788,489 A | 8/1998 | Huffman | |
| 5,788,490 A | 8/1998 | Huffman | |
| 5,800,166 A | 9/1998 | Huffman | |
| 5,807,099 A | 9/1998 | Johnson | |
| 5,868,569 A | 2/1999 | Huffman | |
| 5,934,901 A | 8/1999 | Huffman | |
| D429,815 S | 8/2000 | Huffman | |
| 6,106,284 A | * 8/2000 | Cronin et al. | 433/34 |
| D430,672 S | 9/2000 | Huffman | |
| D433,754 S | 11/2000 | Huffman | |
| D443,363 S | 6/2001 | Huffman | |
| D444,559 S | 7/2001 | Huffman | |
| D452,009 S | 12/2001 | Huffman | |
| D452,010 S | 12/2001 | Huffman | |
| D452,319 S | 12/2001 | Huffman | |
| D452,320 S | 12/2001 | Huffman | |
| D452,321 S | 12/2001 | Huffman | |
| D452,322 S | 12/2001 | Huffman | |
| D452,566 S | 12/2001 | Huffman | |
| D452,567 S | 12/2001 | Huffman | |
| D452,568 S | 12/2001 | Huffman | |
| D456,902 S | 5/2002 | Huffman | |
| D456,903 S | 5/2002 | Huffman | |
| D456,904 S | 5/2002 | Huffman | |
| D457,243 S | 5/2002 | Huffman | |
| D457,636 S | 5/2002 | Huffman | |
| D457,637 S | 5/2002 | Huffman | |
| D457,963 S | 5/2002 | Huffman | |
| D457,964 S | 5/2002 | Huffman | |

* cited by examiner

DENTAL MODEL BASE CONFIGURED FOR CUSTOMIZED APERTURE FORMATION

CROSS REFERENCE TO RELATED APPLICATIONS

This application is a continuation-in-part of U.S. Ser. No. 09/349,192 filed on Jul. 7, 1999 now abandoned which is herein incorporated by reference.

BACKGROUND OF THE INVENTION

1. Field of Invention

This invention relates to dental model bases and methods of forming dental models.

2. Related Art

A successful repair of damaged teeth either by bridge inlays, replacement by crowns, or other common dental prostheses requires accurate alignment and visual uniformity of the repaired tooth with the patient's other teeth. Typically a model is made of the patient's teeth and the prosthesis is fitted to the model and adjusted to achieve proper alignment and visual uniformity.

The model is typically formed by having the patient bite into a pliant casting material that cures to create a mold cavity having a negative impression of the patient's teeth and gums. The mold can be of all or any portion of the patient's gum line. A castable material is then poured into the negative impression to create a stone replica of dental model of the patient's teeth and gums.

To facilitate prosthesis development, the replica of the damaged tooth or teeth is severed from the remainder of the dental model. Severability is achieved by positioning the tapered end of the dowel pin in an aperture formed in the dental model base that corresponds to the damaged tooth or teeth. Typically, the aperture is formed as part of the dental model base during manufacture or is formed in a cast stone base by allowing the stone to cure around a pin. The knurled end of a tapered dowel pin is placed in the stone material in the negative impression in correspondence with the damaged tooth or teeth. To prevent bonding of the damaged tooth model with the dental model base, wax may be placed between the dental model base and the dental model.

Once the dental model has cured, a saw cut on each side of the damaged tooth model is made down to the dental model base that allows removal of the damaged tooth model and attached dowel from the rest of the dental model. After the damaged tooth model is removed, the prosthesis can be fitted and adjusted without the spatial limitations encountered when the damaged tooth model is joined to the full dental model. After the prosthesis is made and attached to the dental model segment, the tapered dowel, dowel pin or pins attached to the dental model segment is guided into the respective premanufactured aperture or apertures, in the dental model base which determines the dental model segment in the dental model. Alignment and visual conformity are then assessed.

Alignment is ascertained by evaluating the registration of the repaired tooth with the dental model of the patient's opposing teeth. This is achieved by connecting the upper and lower dental model with an articulator. In some situations, a disposable articulator such as the Vertex® articulator is preferred. In other situations, a traditional metal articulator is preferred. If the prosthesis is out of alignment or does not visually conform to the rest of the patient's teeth, the dental model segment containing the damaged tooth can be removed, adjusted and returned to the dental model base. This process is repeated until proper alignment and visual conformity are achieved. Thus, the model of the damaged tooth may be repeatedly engaged and disengaged with the dental model base.

SUMMARY OF THE INVENTION

A dental model base is provided. The dental model base includes a dental model base body having a dental model support surface. The dental model support surface is adapted for formation of an aperture corresponding to a model of a specific damaged tooth. The dental model base body is also configured to be disengagably connected to an articulator attachment plate.

In accordance with another aspect of the invention a dental model base is provided having a dental model support surface. The dental model support surface is adapted for the formation of an aperture corresponding to a model of a specific damaged tooth. The dental model base is also configured to be disengagably connected to a disposable articulator.

In accordance with another aspect of the invention a dental model base is provided having a dental model support surface configured for formation of apertures. The dental model base includes a dental model base body having a first end and a second end. The end has a receiver socket adapted to engage a ball. The first end also has a slot adapted to engage a disposable articulator.

In accordance with another aspect of the invention, a kit is provided comprising a dental model base body having a support surface configured for the formation of apertures. The dental model base is configured to be disengagably connected to an articulator attachment plate. The kit further includes an articulator attachment plate.

In accordance with another aspect of the invention, a method of detachably connecting a model of a damaged tooth to an articulator is provided. The method includes casting a negative impression of at least a portion of a patient's teeth. The method includes identifying on the support surface the desired location of a pin to support a model of a damaged tooth. An aperture is created in the support surface corresponding to the desired pin location. A pin is placed in the aperture so that a first end extends from the support surface. The method further comprises placing the dental model support surface into the casting material and curing the casting material. The dental model and dental model base are removed from the impression. The method further includes cutting adjacent the model of the damaged tooth so that the damaged tooth may be separated from the dental model.

BRIEF DESCRIPTION OF THE DRAWINGS

The invention may be more completely understood in consideration of the following detailed description of various embodiments of the invention in connection with the accompanying drawings, wherein like numerals represent like parts throughout several views, in which.

Figure 1:
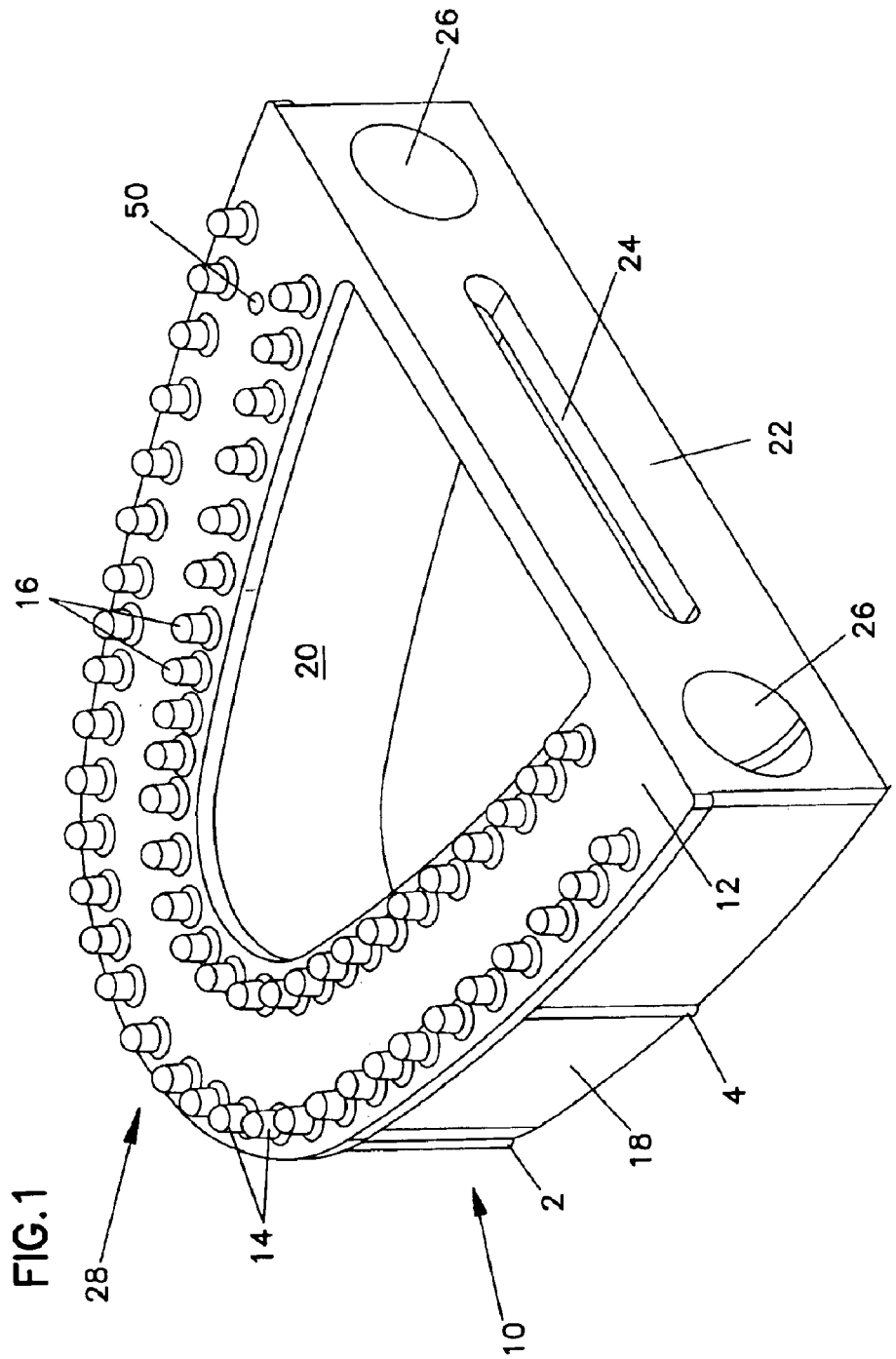
FIG. 1 is a perspective view of an embodiment of a dental model base of the present invention.

While the invention is amenable to various modifications and alternative forms, the specifics thereof have been shown by way of example in the drawings and will be described in detail. It should be understood, however, that the intention is not to limit the invention to particular embodiments described. On the contrary, the invention is to cover all modifications, equivalents, and alternatives falling within the spirit and scope of the invention.

DETAILED DESCRIPTION OF THE PREFERRED EMBODIMENT

The present invention is believed to be applicable to dental models and dental model bases for mounting dental models. In particular, the present invention is directed to a dental model base having a base body that is configured to mount a dental model and is further configured to be disengagably connected to an articulator attachment plate. While the present invention may not be so limited, an appreciation of various aspects of the invention will be gained through a discussion of the examples provided below.

FIG. 1 depicts a dental model base 10 according to one embodiment of the present invention. The dental model base may be constructed of any material or set of materials sufficiently strong and rigid to support a dental model. The dental model base may be constructed of, for example, a polycarbonate material such as Lexan® brand polycarbonate material by General Electric Company. The dental model base may also be made of other materials such as polymers, ceramics, metals, metal alloys, stone, fiberglass, composites, or the like. As shown in FIG. 1, the dental model base 10 has a dental model support surface 12. The shape of the dental model support surface 12 follows the general contours of normal gums. The dental model base 10 is configured to support a full arch dental model.

On the outside of the dental model base 10 there is a positive protrusion 2 that is the location marker for the cuspid and a positive protrusion 4 that is the location marker for the first molar (See FIG. 1). While protrusions shown here correspond to the cuspid and first molar locations, it should be understood that the aligning of the impression with the dental model base may be achieved with a marking on any other location of the dental model base. The protrusions are aligned with the marks on the impression during the pouring stage. The dental model base 10 is held in it's final position over the impression and the teeth locations are marked on the inside of the plastic base in preparation for drilling the hole 50 to receive the metal dowel pin 104 (See FIGS. 1 and 10). It is noted that the alignment for the dental model base with the impression can utilize any form of marking. The marking does not have to be a protrusion on the dental model base. The marking may be an indentation or a painted or colored marking or any other form of identifying a location that can be aligned with a marking on the impression. Likewise, the marking on the impression can take any form that allows a location to be identified.

In the embodiment dental model base shown in FIG. 1, a plurality of tapered pins 14, 16 are formed with the dental model base support surface 12. In this embodiment of the invention, there is a line of indexing pins 16 arranged along the inner periphery of the dental model support surface 12 and a line of indexing pins 14 along the outer periphery of the dental model support surface 12. The pins 14, 16 may be formed of the same material as the dental model base 10 and model support surface 12. The pins 14, 16 may releasably engage a cast dental model.

The external wall 18 extends from the dental model support surface 12 on the opposite side of the support surface from the external line of pins 14 (See FIG. 1). The external wall 18 generally follows the periphery of the dental model support surface 12. An internal wall 20 extends from the dental model support surface 12 on the opposite side of the dental model support surface from the internal line of pins 16. The internal wall 20 generally follows the periphery of the dental model support surface 12. A rear portion 22 of the dental model base 10 includes an articulator attachment groove 24 and two hemispheric sockets 26.

Figure 4:
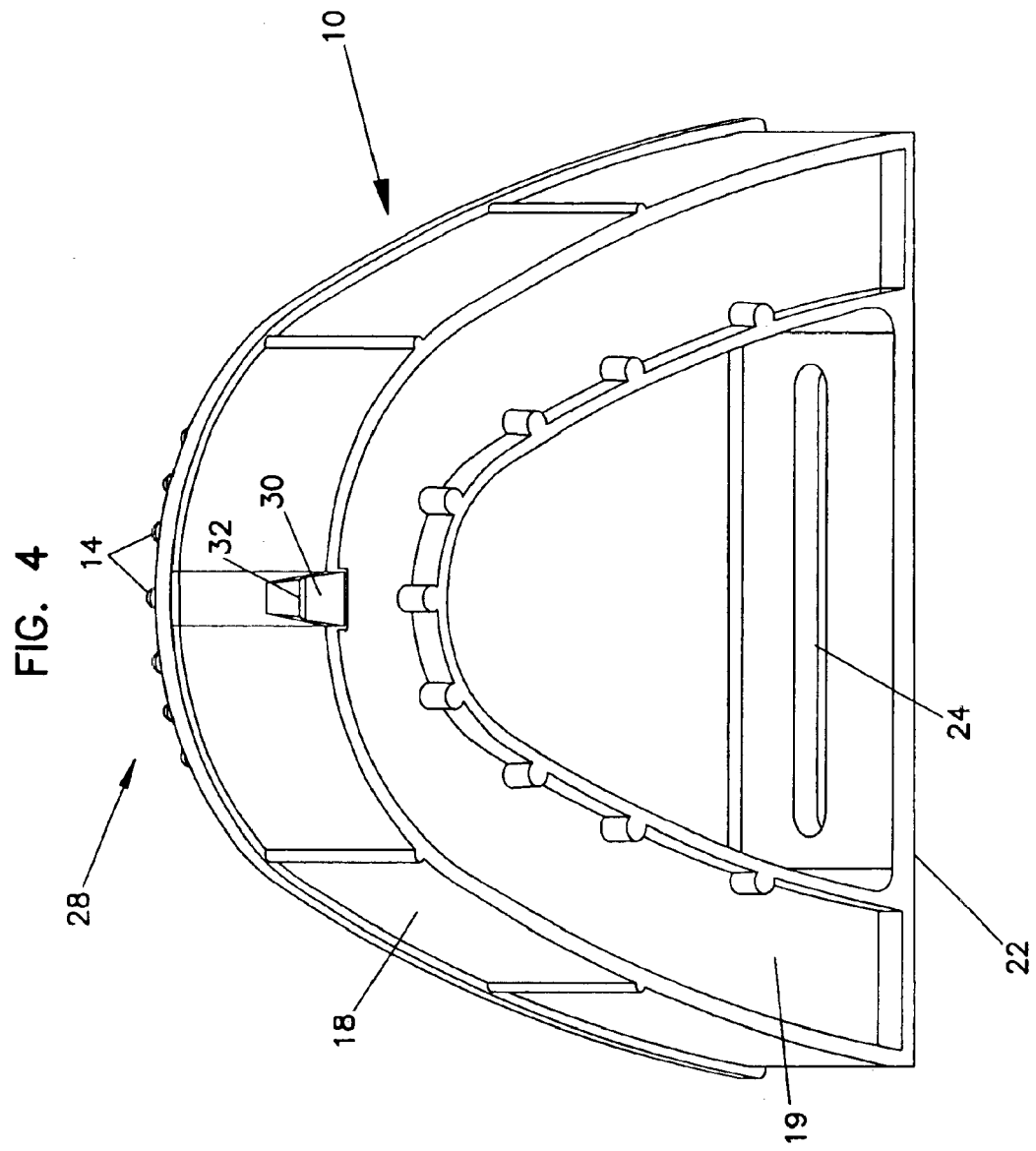
FIG. 4 is a bottom perspective view of an embodiment of a dental model base of the present invention.
Figure 6:
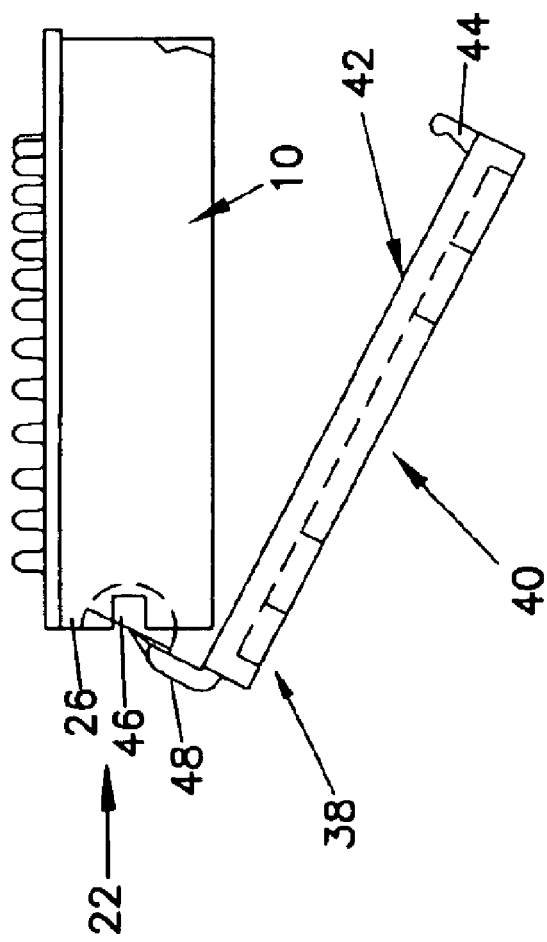
FIG. 6 is a side view of a dental model base and attachment plate according to the present invention.

As shown in FIG. 4, the front 28 of the dental model base 10 has a recess 30 forming a notch 32 to which an articulator attachment plate 38 may be disengagably attached, as shown in FIG. 6.

Figure 5:
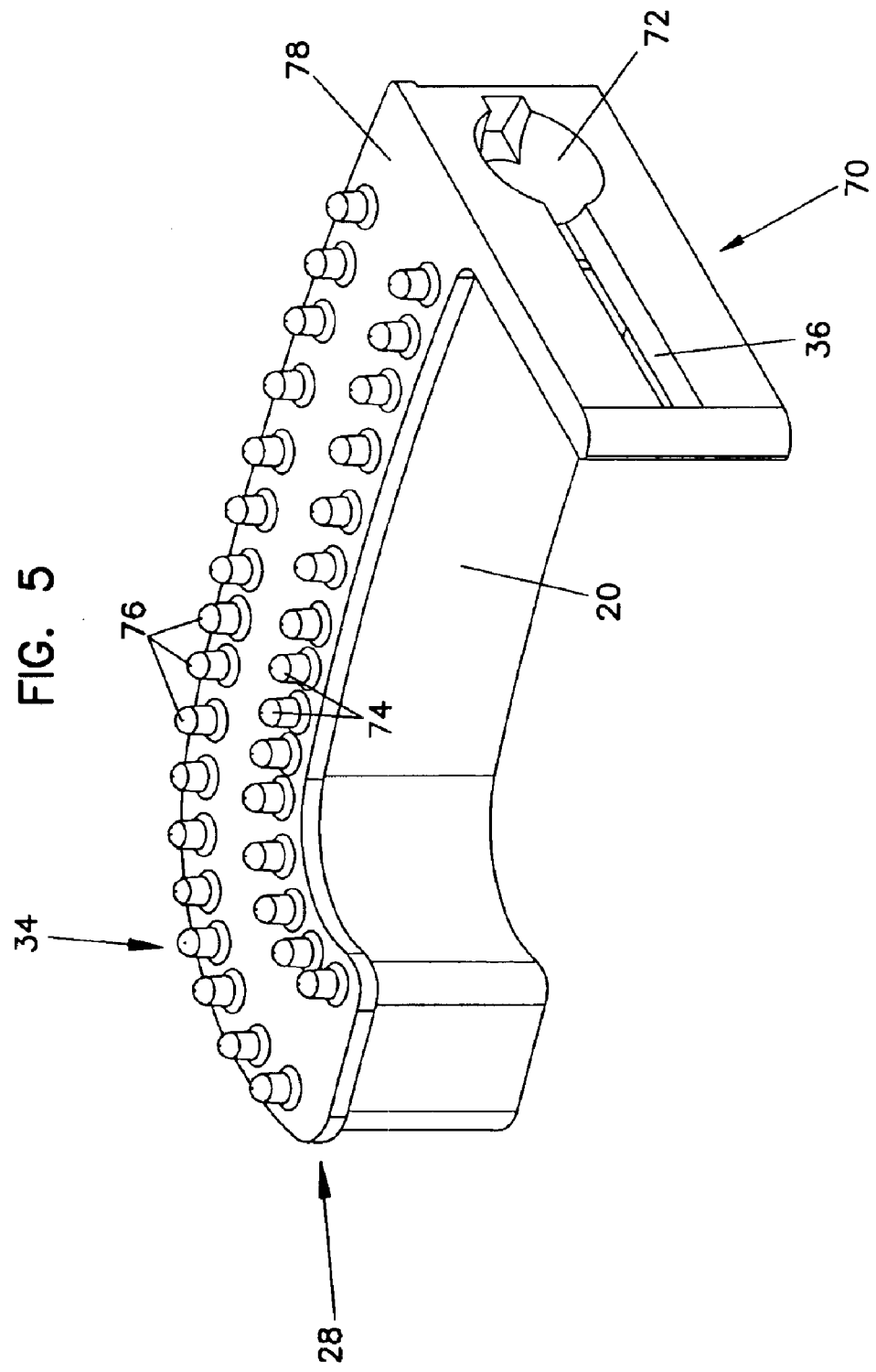
FIG. 5 is a perspective view of a further alternative embodiment of the present invention.

FIG. 5 depicts a base 34 configured to support a quadrant arch dental model. As shown, the quadrant arch base 34 has a socket 72 at the rear 70 of the quadrant arch base 34. The rear 70 of the quadrant arch base 34 has an articulator attachment groove 36 formed across a hemispheric socket 72. In other embodiments, the attachment groove 36 is formed at the rear 70 of base 34, but is not formed across socket 72. In this embodiment, there is an internal line of pins 74 and an external line of pins 76 on the model support surface 78. The external line of pins 76 generally following the periphery of the dental model support surface 78.

FIG. 6 is a perspective view of an embodiment of the present invention. An articulator attachment plate 38 has an articulator attachment side 40 and a base engagement side 42. A hook 44 is at one end of the attachment plate 38. A hemisphere or ball 46 is connected to the opposite end of the attachment plate 38 by a hemisphere connecting member 48. The attachment plate 38 is connected to the base 10 by placing the hemisphere or ball 46 in the socket 26 formed in the rear 22 of the base 10, as shown in FIG. 6. The attachment plate is then rotated about the ball 46 and socket 26 relative to the base 10.

Figure 7:
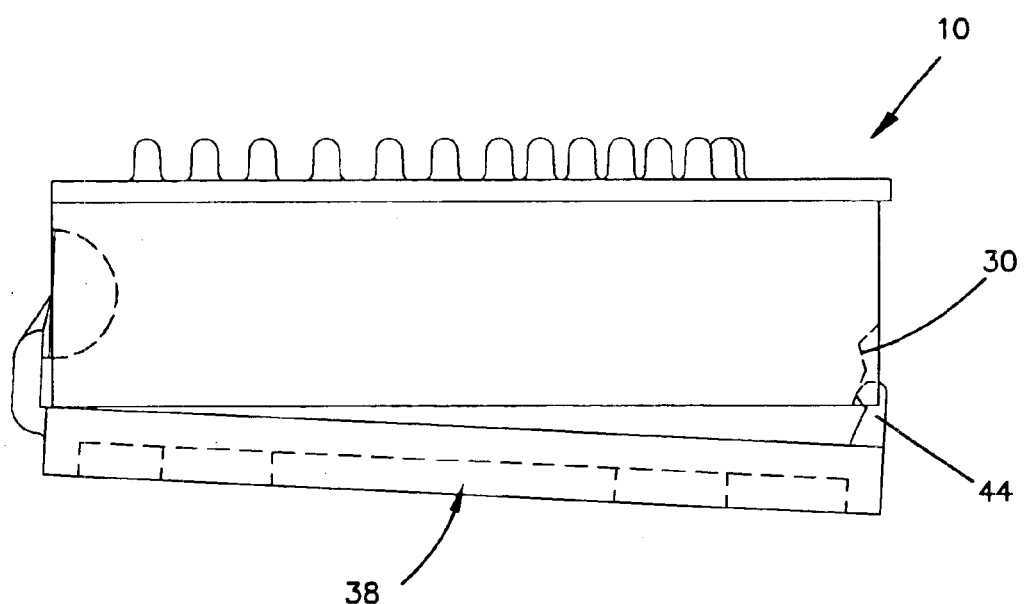
FIG. 7 is a side view of a dental model base and attachment plate according to the present invention.
Figure 8:
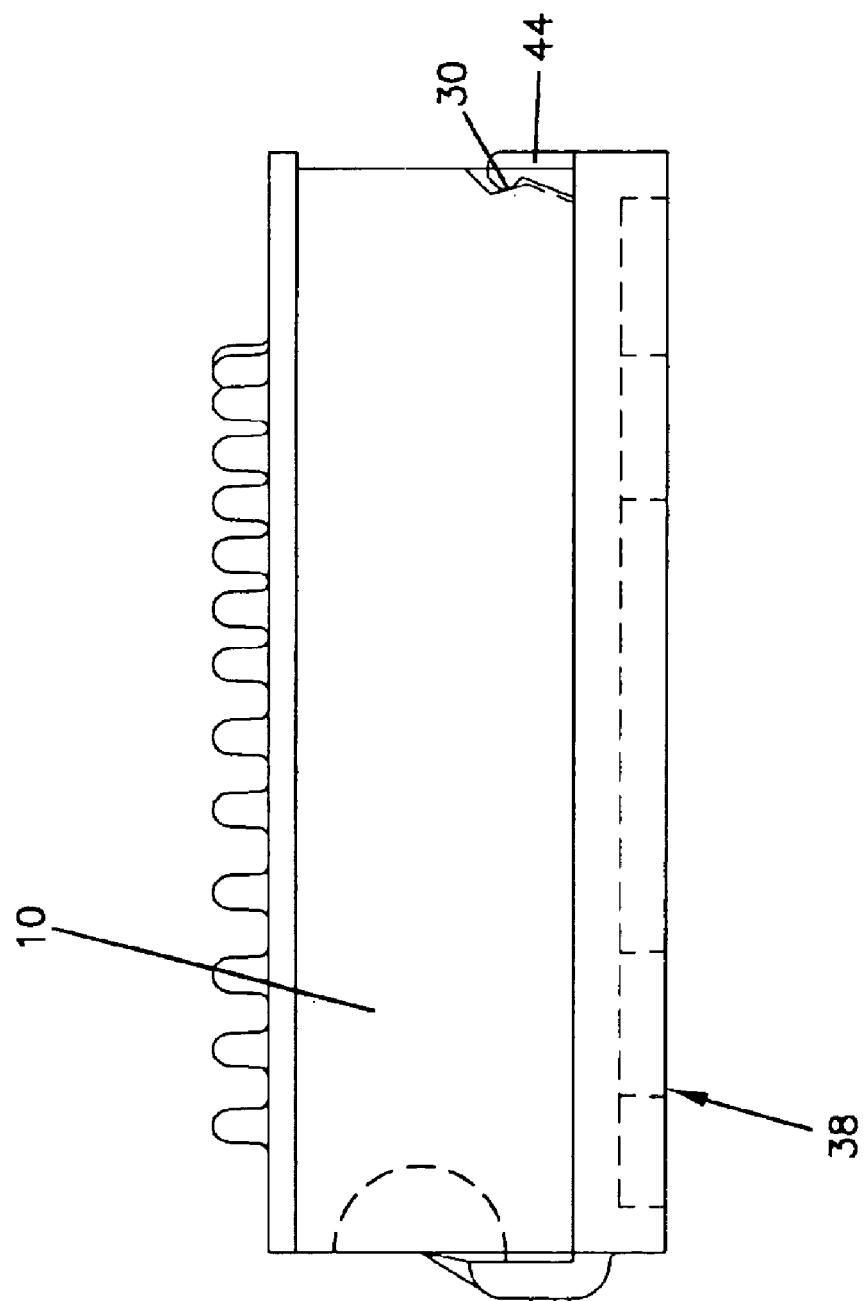
FIG. 8 is a side view of a dental model base and attachment plate according to the present invention.

As shown in FIG. 7 the hook 44 slidingly engages the recess 30 in the base 10. As pressure is applied to join the base 10 and the attachment plate 38, the hook 44 slides along an inclined plane of the recess 30. When the attachment plate 38 is properly engaged with the base 10, as shown in FIG. 8, the hook 44 engages the recess 30 and secures the attachment plate 38 to the base 10.

Figure 11:
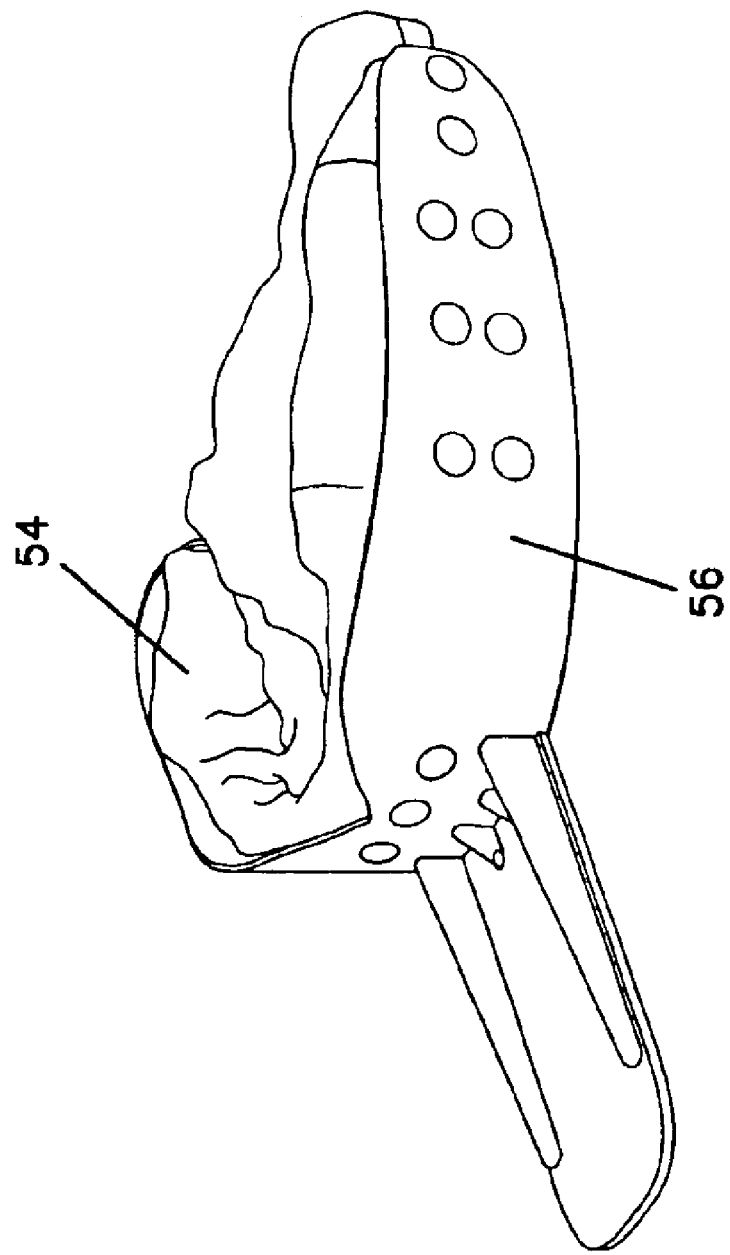
FIG. 11 is a perspective view of an impression and a holder.

The model is typically formed by having a patient bite into a pliant casting material that cures to create a mold cavity having a negative impression of the patient's teeth and gums. An example of a negative impression 54 of the patient's teeth and gums maintained in a holder 56 is shown in FIG. 11. The mold can be of all or any portion of the patient's gum line. Any excess impression material or any material that would interfere with the proper positioning of the model base may be removed, while being careful not to remove any material that is needed to maintain the integrity of the impression. The cuspid and first molar locations are marked on the impression as a reference for positioning the dental model base.

Figure 2:
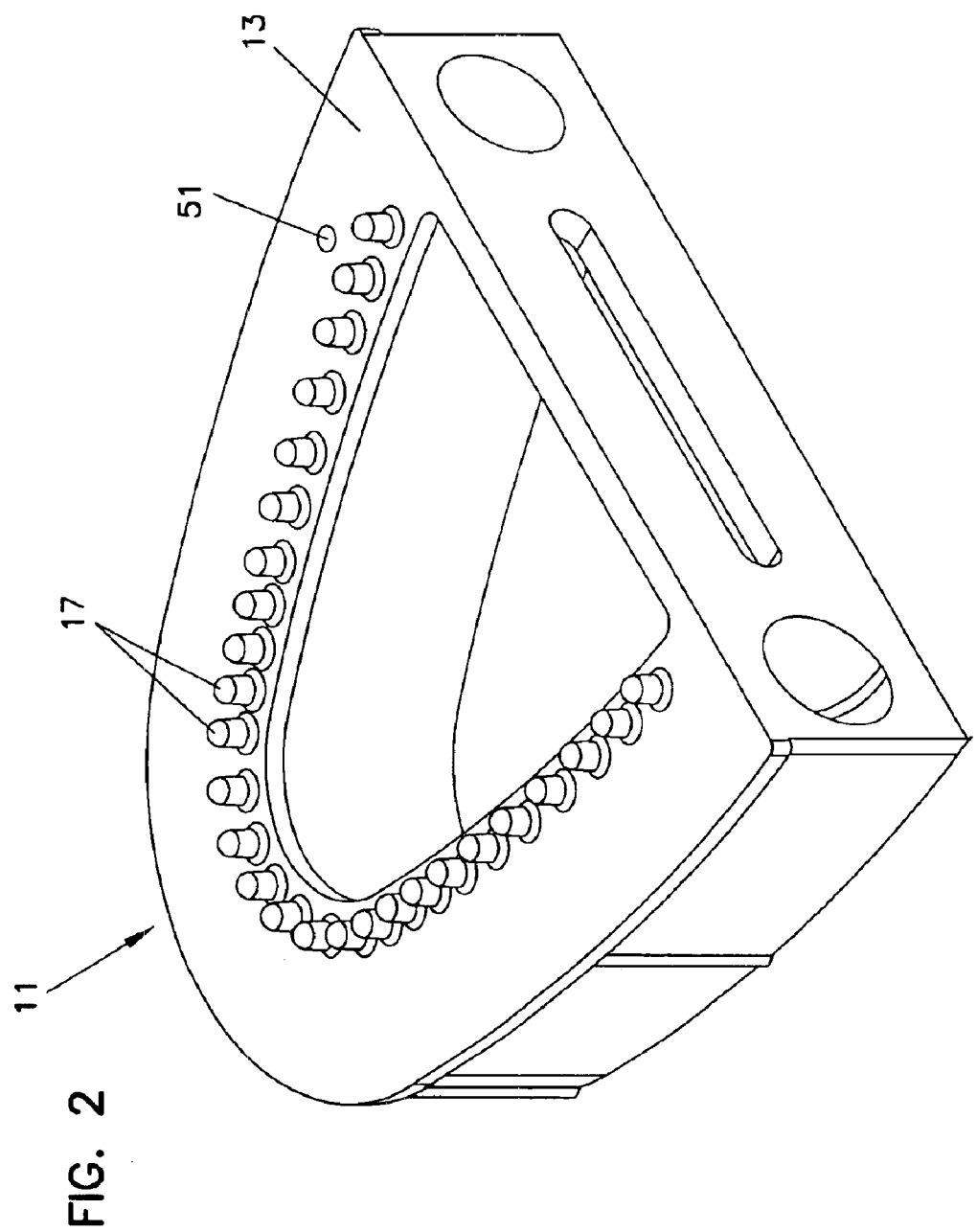
FIG. 2 is a perspective view of an alternative embodiment of a dental model base of the present invention.

A dental model support surface 12 may include any type of pin construction or alternatively no pins at all. For example, an alternative embodiment of the present invention is shown in FIG. 2 showing an alternative configuration of pins 17 protruding from the dental model support surface 13. Thus if desired, the dental model base support surface 13 of the dental model base 11 can have a single row of pins 17. In this embodiment a hole 51 may be drilled or otherwise formed in the dental model support surface 13 is required by the technician to receive the dowel pin 104 (See FIGS. 2 and 10).

Figure 3:
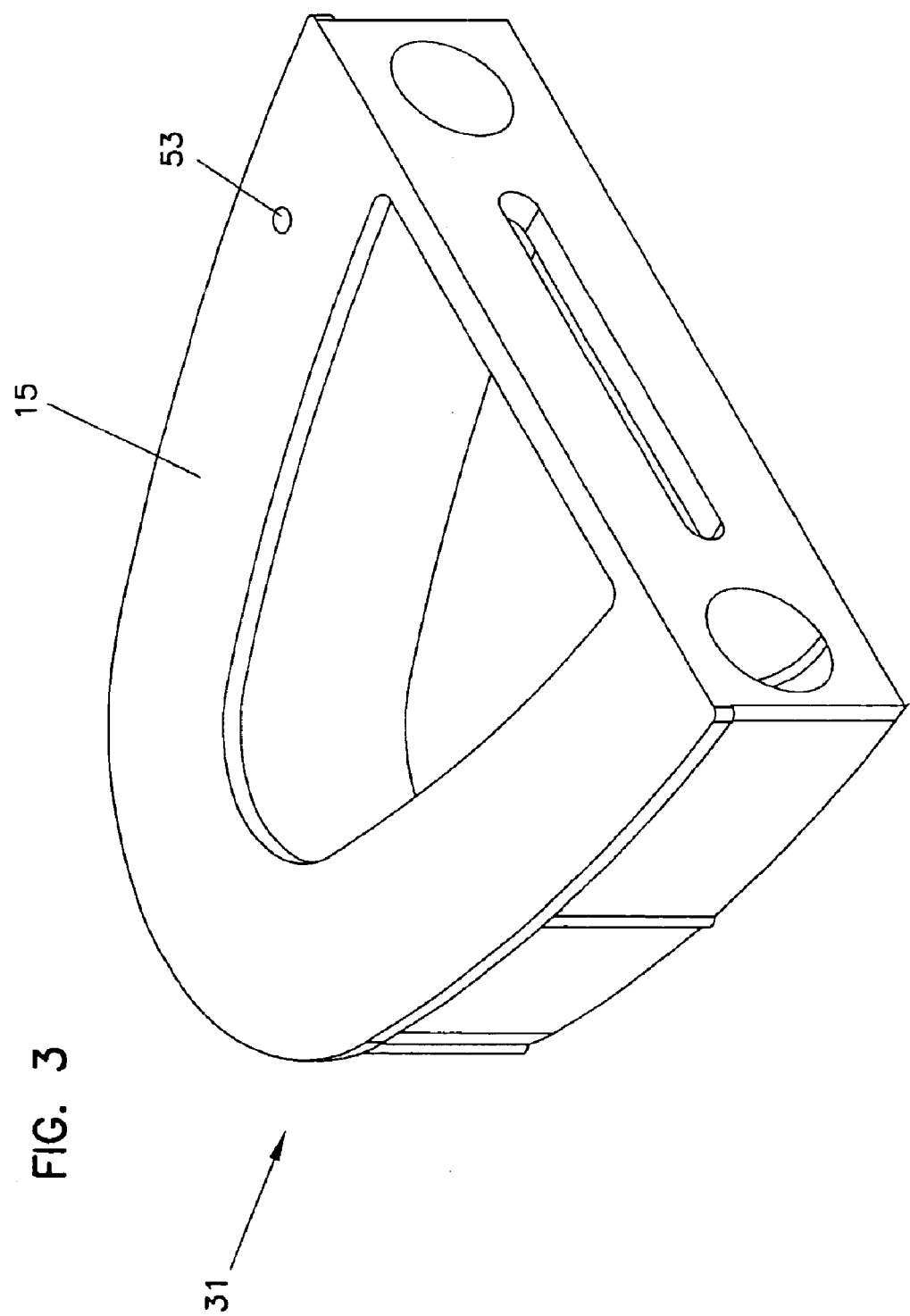
FIG. 3 is a perspective view of a further alternative embodiment of a dental model base of the present invention.

FIG. 3 is a further alternative embodiment showing a dental model base 31 with a dental model support surface 15 with no preformed pins. In this embodiment, a hole 53 can be drilled or otherwise formed in the dental model base support surface 15 by the technician to receive the metal dowel pin.

A dental model base 10 according to the present invention may be used with the mold cavity such that a technician can drill or form at least one aperture 50 in the dental model base support surface 12 corresponding to the location of a damaged tooth or teeth. The apertures may have a taper, such as for example, a two-degree taper (See FIG. 1).

Figure 10:
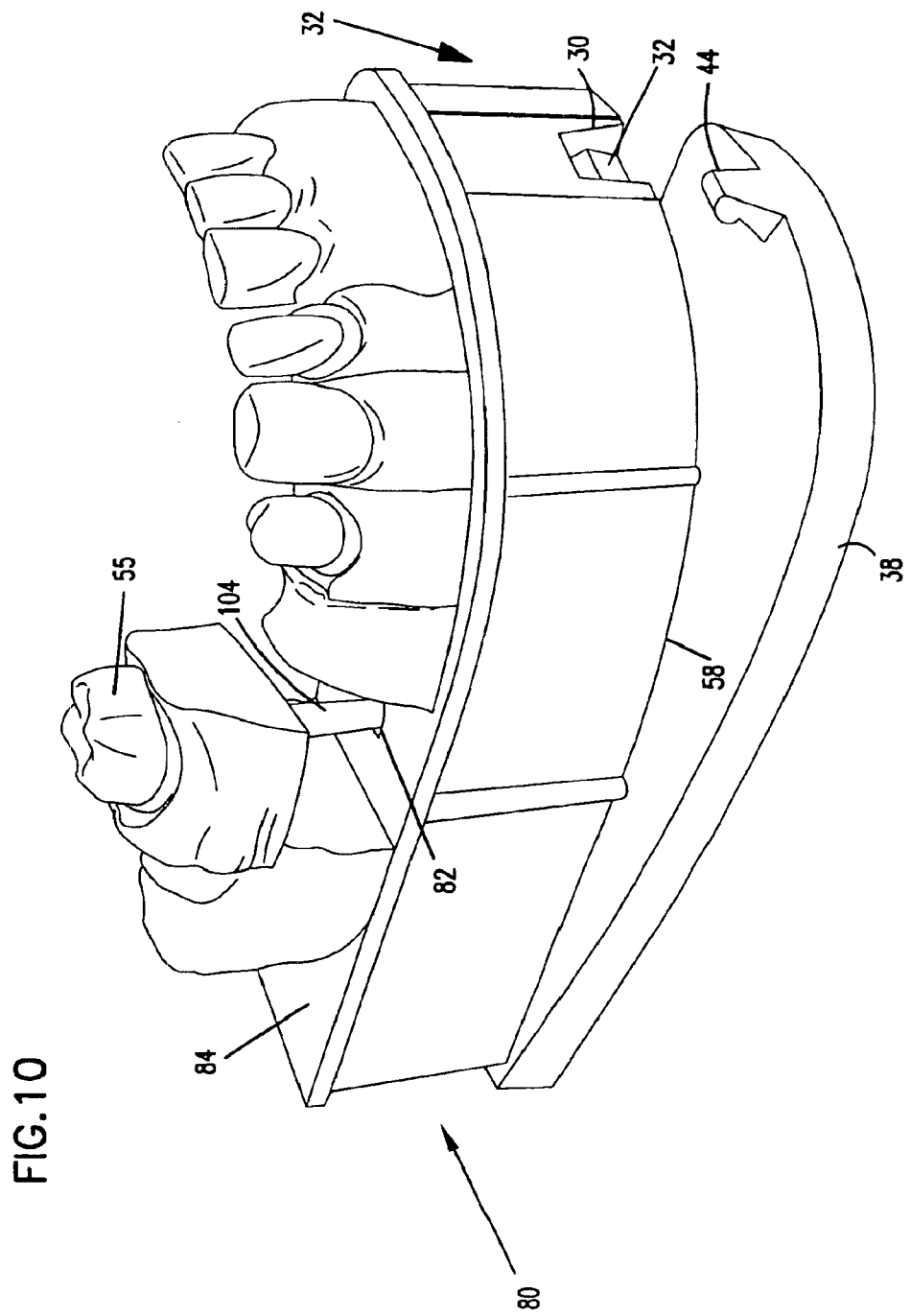
FIG. 10 is a perspective view showing an attachment plate and a dental model base according to the present invention.

FIG. 10 shows a dental model base 80 that is held in its final position over the impression and the teeth locations are marked on the inside of the dental model base 80 in preparation for drilling or otherwise forming a hole 82 to receive the metal dowel pin 104. If desired, the hole 82 is drilled into the dental model base 80 at each marked location. A metal pin is not needed for every tooth and only the teeth that will be needed in the fabrication of the dental prosthesis are pinned.

A tapered metal dowel pin 104 is inserted into each drilled aperture 82 or apertures, in the dental model support surface 84 with enough pressure to insure that it will not become dislodged during the pouring process (See FIG. 10). The dowels typically have a two-degree taper on one end and knurling on the opposite end. The tapered end slidingly engages the apertures drilled in the dental model support surface and the knurled end is aligned with the negative impression of a tooth or teeth.

A castable material is then poured into the negative impression to create a stone replica or dental model of the patient's teeth and gums. First, the model stone is vacuum mixed with water to a thick, creamy mix. Next, the impression is held on a vibrator while the stone mix is teased into each tooth cavity. Further, the impression is filled to a level of ¼ to ⅜ of an inch above the margin or shoulder line of the teeth. A small amount of mix is teased around the knurled portion of the metal pins and also the plastic index pins that are sticking up from the surface of the base. The knurled end of a tapered dowel pin or pins protrudes from the dental model support surface and is positioned in the uncured stone material in correspondence with the damaged tooth or teeth by positioning the base and pin assembly adjacent the uncured dental model. Pins may be placed under other parts of the model at the discretion of the dental technician.

The dental model base 10 is then lowered into the impression while making sure to maintain proper alignment and position via the marks made prior to pouring. Any excess stone that is displaced may be very carefully removed. This will reduce the amount of stone that will need to be ground or trimmed after the stone has hardened. After the impression stone has hardened enough (usually about 20 to 30 minutes) then a mix of base stone 58 is poured into the plastic model base around the tapered portion of the pins and allowed to harden (See FIG. 10). Hardened stone model with plastic base attached is removed from the impression. Unneeded stone is trimmed away up to the model support surface 84. Necessary teeth are sectioned and removed by carefully tapping the small end of the metal pin. Then each tooth preparation is trimmed to expose the margins at gum line in preparation for waxing.

Figure 9:
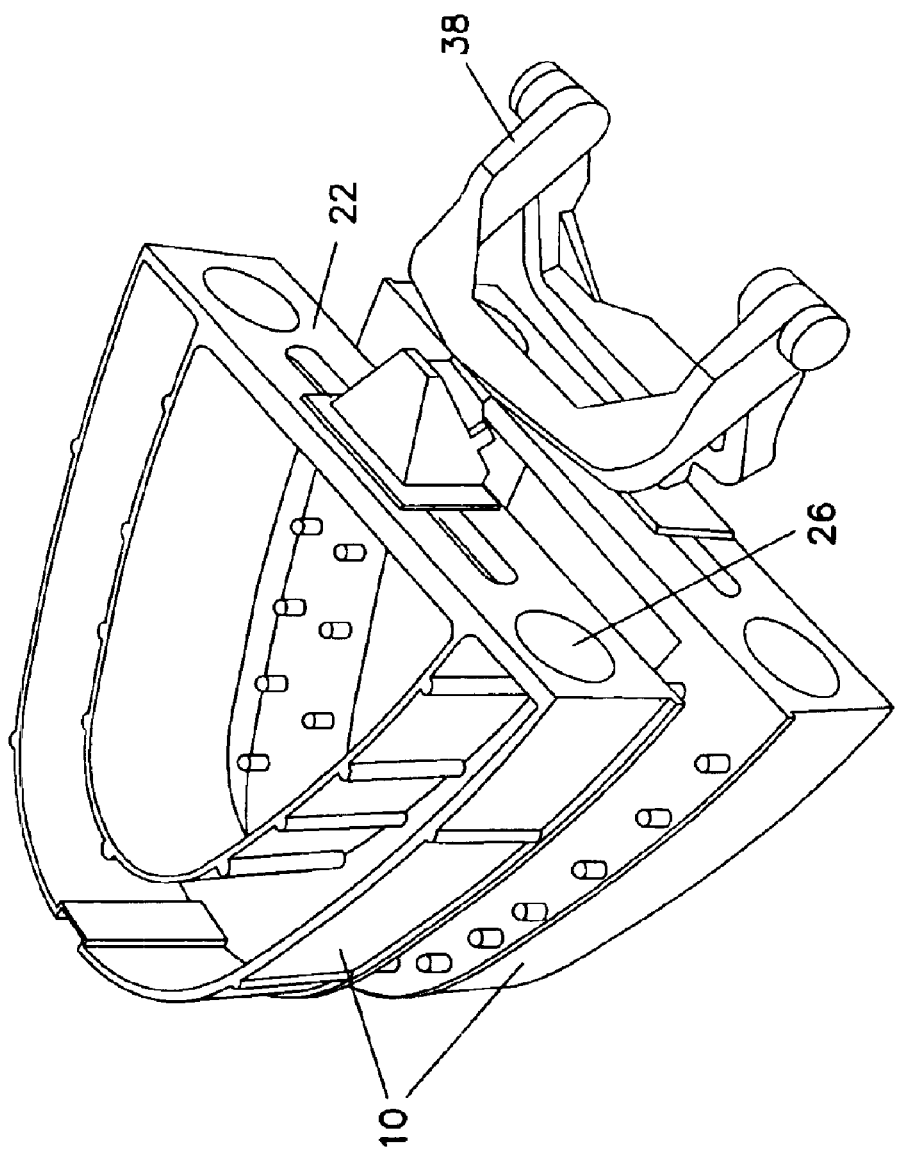
FIG. 9 shows a disposable articulator connected to two dental model bases of the present invention.

Once the dental model is cured the mold may be removed. In one embodiment, shown in FIG. 10, the dental model segment of a damaged tooth 55 is disengagably connected to the dental model base. If desired, the dental model base may then be connected to a disposable articulator as depicted in FIG. 9. As shown, a tongue of the disposable articulator engages the rear portion of the dental model base. Alternatively, a ball at each end of the disposable articulator could engage a socket at the ends of the dental model base. The same dental model base may also be connected to a traditional metal articulator.

The foregoing describes various embodiments of the claimed invention. The claimed invention is not limited to the embodiments described above. For example, it is contemplated that the principles of the invention described above can be applied to full arch dental model bases and quadrant model bases. It is also contemplated that this invention can be adapted for use with a variety of upper and lower gum sizes. Thus, numerous alternative constructions exist that would fall within the scope of the claimed invention.

I claim:

1. A dental model base comprising a dental model base body, the dental model base body comprising:
    (a) a dental model support surface said dental model support surface being configured for the formation of an aperture corresponding to a model of a specific damaged tooth, wherein the aperture is formable in the dental model support surface only after a mold of the specific damaged tooth is aligned with the dental model support surface to determine a proper location on the dental model support surface for formation of the aperture, said dental model support surface being void of preformed apertures therein that are suited for mounting said model to said dental model base;
    (b) an internal wall extending from said dental model support surface; and
    (c) an external wall extending from said dental model support surface and at least partially defining opposing first and second end walls of the dental model base, at least one of the first and second end walls being configured to be disengagably connected to an articulator attachment plate.

2. The dental model base of claim 1 wherein the first end wall includes a socket adapted to engage a ball of an articulator attachment plate.

3. The dental model base of claim 2 wherein the second end wall of the dental model base body comprises a notch configured to engage the articulator attachment plate.

4. The dental model base of claim 1 wherein said first end wall is further configured to be disengagably connected to a disposable articulator.

5. The dental model base of claim 4 wherein the first end wall includes a slot adapted to engage a disposable articulator.

6. The dental model base of claim 1, wherein said aperture is formable in a multitude of positions on said dental model support surface as required to properly engage teeth in a variety of positions.

7. A dental model base comprising a dental model base body, the dental model base body comprising:
  (a) a dental model support surface adapted for the formation of an aperture corresponding to a model of a specific damaged tooth, said aperture being formable in a multitude of positions on said dental model support surface as required to properly engage said model in a variety of positions, said dental model support surface being void of preformed apertures therein that are suited for mounting said model to said dental model base until after the aperture corresponding to the model of the specific damaged tooth is formed in the dental model support surface;
  (b) an internal wall extending from said dental model support surface;
  (c) an external wall extending from said dental model support surface, said dental model support surface extending between the internal and external walls; and
  (d) a first end and a second end each defined at least partially by said external wall or said internal wall, wherein one of the first and second ends is configured to be disengagably connected to a disposable articulator.

8. The dental model base of claim 7 wherein said first end includes a slot adapted to engage a disposable articulator.

9. A dental model base comprising a dental model base body comprising:
  (a) a dental model support surface having a continuous surface configured for the formation of apertures;
  (b) an internal wall extending from said dental model support surface;
  (c) an external wall extending from said dental model support surface;
  (d) a first end and a second end, said first end having a receiver socket adapted to engage a ball, and said first end having a slot adapted to engage a disposable articulator.

10. The dental model base of claim 9 wherein the dental model base is manufactured from polycarbonate material.

11. The dental model base of claim 10 wherein said polycarbonate material is Lexan® polycarbonate material.

12. The dental model base of claim 9 wherein said dental model support surface includes a plurality of indexing pins protruding from the dental model support surface, said pins adapted to slidingly engage a case dental model.

13. A dental model base kit comprising:
  (a) a dental model base body configured to be disengagably connected to an articulator attachment plate, the dental model base body comprising:
    (i) a generally vertically oriented internal wall;
    (ii) a generally vertically oriented external wall; and
    (iii) a dental model support surface extending between the internal and external walls and being configured for the formation of an aperture corresponding to a tooth in a dental model, wherein the aperture is formable in the dental model support surface only after a mold of the specific damaged tooth is aligned with the dental model support surface to determine a proper location on the dental model support surface for formation of the aperture, said dental model support surface being void of preformed apertures therein that are suited for mounting said model to said dental model base; and
  (b) an articulator attachment plate configured to be disengagably connected to the internal or external wall of the dental model base body.

14. A method of forming a dental model including a detachable model of a damaged tooth, the method comprising:
  casting a negative impression of at least a portion of a patient's teeth, said impression including an impression of said damaged tooth;
  providing a dental model base having a generally vertical internal wall, a generally vertical external wall, and a dental model support surface extending horizontally between the internal and external walls, the dental model support surface comprising a rigid or semi-rigid material;
  identifying on the dental model support surface the desired location of a pin to support a model of said damaged tooth;
  drilling an aperture in said dental model support surface corresponding to said desired pin location;
  placing a pin in said aperture, said pin having a first end extending from said dental model support surface;
  placing casting material into said negative impression;
  placing said dental model support surface into said casting material while maintaining proper alignment and position such that said pin first end extends into said casting material;
  curing said casting material to form a dental model including a model of said damaged tooth;
  removing the dental model with dental model base attached from the impression; and
  cutting adjacent said model of said damaged tooth such that said model of said damaged tooth may be separated from said dental model, said model of said damaged tooth being connected to said pin, said pin being slidingly engageable with said aperture in said dental model support surface.

15. The method of claim 14 wherein identifying on the support surface the desired location of a pin further comprises:
  marking the impression with at least one reference point for positioning the dental model base;
  placing a dental model base adjacent said negative impression, said dental model base having a continuous dental model support surface; and
  marking the support surface to identify the desired location of a pin to support a model of said damaged tooth.

16. The method of claim 14 further comprising:
  connecting an articulator attachment plate to an articulator; and
  detachably connecting said articulator attachment plate to said dental model base.

17. The method of claim 14 wherein said dental model support surface includes indexing pins.

18. The method of claim 14 wherein creating the aperture comprises drilling the aperture.

19. The method of claim 14 wherein said aperture has a two degree taper.

20. The method of claim 14 wherein said dental model base is connectable to a disposable articulator.

21. The method of claim 14 wherein said dental model base includes a spherical cavity at a first end and a notch at the second end.

22. The method of claim 14 further comprising removing excess impression material from the impression.

23. A method of preparing a dental model base that is configured for supporting a dental model formed from a mold of a patient's teeth, the method comprising:

providing a dental model base having a generally vertical internal wall, a generally vertical external wall, and a dental model support surface extending horizontally between the internal and external walls and defining a support surface of the dental model base that engages a mold of a patient's teeth and defines an outermost surface of the dental model base, the dental model support surface comprising a rigid or semi-rigid material, the external and internal walls and the dental model support surface being formed as a unitary piece;

identifying on the dental model support surface a desired pin location; and forming an aperture in said dental model support surface corresponding to said desired pin location after identifying the desired pin location.

24. The method of claim 23, further comprising placing a pin in said aperture, said pin having a first end extending from said dental model support surface.

25. The method of claim 23, further comprising forming at least one fixed indexing pin on the dental model support surface.

26. The method of claim 23, further comprising forming at least one row of fixed indexing pins on the dental model support surface.

27. The method of forming a dental model base configured for supporting a model of a patient's teeth, the method comprising:

forming an outer wall;

forming an inner wall;

forming a dental model support surface that extends between the outer wall and the inner wall, the dental model support surface being configured for the formation of an aperture corresponding to a specific tooth of the model, wherein the aperture is formable in the dental model support surface only after a mold of the specific damaged tooth is aligned with the dental model support surface to determine a proper location on the dental model support surface for formation of the aperture, said dental model support surface being void of preformed apertures therein that are suited for mounting said model to said dental model base; and forming at least one attachment structure in the outer wall, the at least one attachment structure being configured to disengagably couple the dental model base to an articulator attachment plate.

28. The method of claim 27, wherein the outer wall defines first and second end walls of the dental model base, and the method includes forming first and second attachment structures in respective first and second end walls.

29. A dental model base body, comprising:

(a) a generally vertically oriented internal wall;

(b) a generally vertically oriented external wall defining an end wall of the dental model base body, the end wall being configured to disengagably connect to an articular attachment plate; and (c) a dental model support surface extending between the internal and external walls and being configured for the formation of an aperture corresponding to a tooth in a dental model, wherein the aperture is formable in the dental model support surface only after a mold of the specific damaged tooth is aligned with the dental model support surface to determine a proper location on the dental model support surface for formation of the aperture, said dental model support surface being void of preformed apertures therein that are suited for mounting said model to said dental model base.

* * * * *